United States Patent [19]
Keller et al.

[11] Patent Number: 5,248,615
[45] Date of Patent: Sep. 28, 1993

[54] CALIBRATOR COMPOSITION FOR PROLACTIN ASSAY

[75] Inventors: Charles H. Keller, Lindenhurst, Ill.; Laura D. Klein, Morristown, N.J.; Inge S. Brynes, Libertyville, Ill.

[73] Assignee: Abbott Laboratories, Abbott Park, Ill.

[21] Appl. No.: 939,963

[22] Filed: Sep. 4, 1992

Related U.S. Application Data

[63] Continuation of Ser. No. 478,115, Feb. 9, 1990, abandoned.

[51] Int. Cl.$^5$ ............... G01N 33/00; G01N 33/50
[52] U.S. Cl. ............................................ 436/15; 436/8; 436/817; 436/826; 435/967
[58] Field of Search ............ 436/8, 15, 18, 518, 436/536, 804, 811, 826; 435/7.92, 7.93, 967

[56] References Cited

U.S. PATENT DOCUMENTS 4,753,888  1/1988  Chiang ............................ 436/11

FOREIGN PATENT DOCUMENTS 337466  10/1989  European Pat. Off. ............. 436/8

OTHER PUBLICATIONS

Nyberg et al., Upsala J. Med. Sci., 90:265–277 (1985).

*Primary Examiner*—Esther L. Kepplinger
*Assistant Examiner*—Carol E. Bidwell
*Attorney, Agent, or Firm*—Richard D. Schmidt

[57] ABSTRACT

A stabilized prolactin calibrator is disclosed. The calibrator has a pH from about 5.5 to about 9.0, and contains prolactin in a 0.01 M to 0.2 M matrix of tris-(hydroxymethyl)aminomethane which additionally contains about 0.3 to 4 percent of bovine serum albumin, about 0.05 to 0.2 percent of sodium azide and from about 0.01 to about 0.2 mole/liter NaCl.

8 Claims, No Drawings

CALIBRATOR COMPOSITION FOR PROLACTIN ASSAY

This application is a continuation of application Ser. No. 07/478,115, filed Feb. 9, 1990, now abandoned.

FIELD OF THE INVENTION

This invention relates to an aqueous calibrator composition for a prolactin assay; the calibrator composition has a shelf life at 2°-8° C. of at least six months.

BACKGROUND OF THE INVENTION

Various analytical procedures and devices are commonly employed in assays to determine the presence and/or concentration of substances of interest or clinical significance which may be present in biological fluids or other materials. Such substances are commonly termed "analytes" and can include antibodies, antigens, drugs, hormones, etc. The detection of particular analytes in biological fluids such as serum, plasma, urine, spinal fluid and the like has in recent years become of critical importance in both research and clinical settings. The detection of analytes of interest can often be related to various disease states and consequently is extremely useful in the diagnosis of disease and in monitoring the effectiveness of therapy. When the analytes are antigens or antibodies, assays typically depend upon the immunological reactivity which characterizes these substances. Generally, such assays are collectively termed immunoassays.

Immunoassay techniques take advantage of the mechanisms of the immune systems of higher organisms, wherein antibodies are produced in response to the presence of antigens which are pathogenic or foreign to the organisms. At least one antibody is produced in response to and is capable of reacting with a particular antigen, thereby creating a highly specific reaction mechanism which can be used in vitro to determine the presence or concentration of that antigen in a biological sample. When immunoassay techniques are used to determine the concentration of an antigen in a biological sample, standards containing different known amounts of the antigen can be prepared and subjected to the same test procedure as the biological sample; the concentration of the antigen in the sample can then be determined by comparing the magnitude of the response (for example, the rate of fluorescence in the case of a known assay for prolactin) obtained from the sample with the magnitude of the responses obtained from the standards.

Immunoassays for the determination of prolactin in blood, serum and the like are known, a synthetic peptide which can be used in such immunoassays being disclosed in U.S. Pat. No. 4,585,740, granted Apr. 29, 1986, and the use of a radio-iodinated hormone stabilized with a non-ionic detergent in such immunoassays being disclosed in U.S. Pat. No. 4,357,310 (see, also, journal articles by Wide, L. et al.: *Immunochemistry* 10 4:381-386, 1967 and *Acta Endocrinol.*, suppl. 174:1-58, 1973).

The aqueous calibrator composition of the instant invention can be used to prepare standards containing different known amounts of prolactin as described above. By determining the rate of fluorescence of the standards, it is possible to prepare a curve of prolactin content as a function of the rate of fluorescence and to determine the prolactin content of a biological sample by comparing its rate of fluorescence with the curve.

It is known that prolactin solutions are unstable in the sense that prolactin assayed after prolonged storage under most storage conditions will be a fraction (often one-half or less) of that before storage. For example, Nyberg et al. (*Upsala J Med Sci* 90:265-277, 1985) report, at p. 274:

"Prolonged storage (2-3 years) at a protein concentration in the range 0.1-2 mg/ml in 0.02 M Tris-HCl buffer (pH 9) at −80° C. neither affected the immunopotency nor altered the electrophoretic pattern of prolactin."

On the same page, the authors present a plot showing that the preserved prolactin activity was less than fifty percent twenty weeks after preparation when stored:

"(d) in 0.02 M Tris-HCl buffer (pH 9.0) at −20° C.
"(e) in 0.01 M ammonium bicarbonate (pH 7.8) at −20° C.
"(f) in 0.02 M Tris-HCl buffer (pH 9.0) containing 0.5 M KCl" (storage temperature not specified).

Because of the instability of prolactin under most storage conditions, it is common practice to furnish lyophilized prolactin, shipped and stored under ambient conditions, and used just before an immunoassay is conducted to prepare calibrators.

THE INSTANT INVENTION

The present invention is based upon the discovery of an aqueous prolactin solution having sufficient stability that it can be shipped and stored for at least as long as six months at 2°-8°. The solutions of the invention are less expensive than lyophilized prolactin and eliminate errors and waste that are often associated with the production of calibrators from lyophilized prolactin.

THE PRIOR ART

Japanese patent publication J56068607, published Sep. 6, 1981, discloses the use of 0.03 to 5.0 percent of a polypeptide obtained by hydrolysis of gelatin or collagen for stabilizing proteins, including prolactin. U.S. Pat. No. 4,806,343, Feb. 21, 1989, discloses that the activity of freeze-dried proteins is improved by the addition, prior to freezing, of a cryogenic protectant which includes a combination of a carbohydrate (trehalose) and a transition metal ion ($Zn^{++}$). U.K. patent application 2,160,528, published Dec. 24, 1985, discloses a water soluble dried composition comprising a protein to be stabilized and a polysaccharide stabilizer mainly composed of repeating maltotriose units.

DESCRIPTION OF THE PREFERRED EMBODIMENT

The following Example, which describes the best mode presently contemplated by the inventors, is presented solely for the purpose of disclosing and explaining the invention, and is not intended to be limiting.

As used herein, and in the appended claims, the following terms, unless otherwise indicated, have the meanings set forth: "percent" and "parts" refer to percent and parts by weight; g means gram or grams; mg means milligram or milligrams; v/v means percent by volume; l means liter or liters; ml means milliliter or milliliters; μl means microliter or microliters; mM means millimolar and equals the number of milligram moles of a solute in 1 liter of a solution; and M means molar and equals the number of moles of a solute in 1 liter of a solution. All temperatures are in °C.

EXAMPLE

A stabilized prolactin calibrator was prepared by adding 30 ng/ml human prolactin to a matrix (pH 7.5) of 0.05 M tris(hydroxymethyl)-aminomethane containing 2 percent of bovine serum albumin ("BSA"), 0.1 mole/liter NaCl and 0.1 percent sodium azide.

A portion of the stabilized prolactin calibrator produced as described in the preceding paragraph was heat stressed at 37° for one week while another portion was stored at 2°-8° for one week. Both portions were then assayed for prolactin. The assay after heat stressing was 101.1 percent of that after storage at 2°-8°, indicating that the heat stressing did not adversely affect the material as a calibrator. A similar result was achieved when the calibrator tested was produced by adding the prolactin to a matrix (pH 6.0) of 0.05M tris(hydroxymethyl)aminomethane containing 2 percent of bovine serum albumin and 0.1 mole/liter NaCl.

For purposes of comparison, but not according to the present invention, various other prolactin solutions containing tris-(hydroxymethyl)-aminomethane ("Tris") or sodium phosphate ("Phos") as a buffer, 30 ng/ml human prolactin, 0.1 mole/liter of NaCl and, in some cases, 0.1 percent of a protein additive, were prepared and a part of each solution was assayed for prolactin after having been heat stressed at 37° for one week while another part was assayed for prolactin after storage for one week at a temperature of 2°-8°. The identity of the buffer in each of these solutions, the pH, the identity of the protein, if any, and the "Percent Span Retention" (100 times the assay after heat stressing divided by the assay after storage for one week at 2°-8°) are set forth in the following table, where "FG" designates fish gelatin.

| Sample Identification | Buffer | Protein additive | pH | % Span Retention |
| --- | --- | --- | --- | --- |
| 1 | Phos | None | 6.0 | 86.1 |
| 2 | Phos | BSA | 6.0 | 89.0 |
| 3 | Phos | FG | 6.0 | 79.5 |
| 4 | Phos | Casein | 6.0 | 79.2 |
| 5 | Phos | None | 7.5 | 87.3 |
| 6 | Phos | BSA | 7.5 | 87.1 |
| 7 | Phos | FG | 7.5 | 74.3 |
| 8 | Phos | Casein | 7.5 | 74.4 |
| 9 | Tris | None | 6.0 | 91.7 |
| 10 | Tris | FG | 6.0 | 57.5 |
| 11 | Tris | Casein | 6.0 | 75.8 |
| 12 | Tris | None | 7.5 | 85.4 |
| 13 | Tris | FG | 7.5 | 91.3 |
| 14 | Tris | Casein | 7.5 | 77.5 |
| 15 | Phos | BSA | 7.5 | 74.7 |
| 16 | Phos | BSA | 7.5 | 82.6 |

Composition 15 also contained 10 millimoles/liter ethylene diamine tetraacetic acid ("EDTA"), and composition 16 also contained 0.15 millimole/liter phenylmethyl sulfonyl fluoride ("PMSF").

Still other prolactin solutions which contained 30 ng/ml human prolactin dissolved in plasma diagnostic base ("PDB"), in horse blood serum, in pig blood serum or in human blood serum, and some which additionally contained EDTA or PMSF, were prepared and were assayed for prolactin after having been heat stressed at 37° for one week and after having been stored for one week at 2°-8°. The prolactin solutions in horse blood serum, pig blood serum and human blood serum all contained 0.1 percent of sodium azide; these serum solutions were produced by allowing whole blood to clot, adding the sodium azide, filtering, and dissolving the prolactin in the filtrate. The PDB solution was prepared from a protein concentrate that is commercially availabale under the designation "Plasma Diagnostic Base"; the solutions were prepared by dissolving 0.2 percent of sodium azide in the PDB, diluting a given volume of the sodium azide solution with an equal volume of distilled water, and dissolving the prolactin in the diluted sodium azide solution. The concentration thereof in solutions which contained EDTA was 10 millimoles/liter; the concentration thereof in solutions which contained PMSF was 0.15 millimole/liter. The identity of the serum in each of these solutions, the identity of the other additive, if any, and the Span Retention are set forth in the following table.

| Sample Identification | Serum | Other Additive | % Span Retention |
| --- | --- | --- | --- |
| 17 | PDB | None | 75.9 |
| 18 | PDB | EDTA | 39.0 |
| 19 | PDB | PMSF | 77.4 |
| 20 | HORSE | None | 69.2 |
| 21 | HORSE | EDTA | 49.9 |
| 22 | HORSE | PMSF | 54.7 |
| 23 | PIG | NONE | 73.4 |
| 24 | PIG | EDTA | 44.9 |
| 25 | PIG | PMSF | 66.1 |
| 26 | HUMAN | NONE | 53.6 |
| 27 | HUMAN | EDTA | 39.6 |
| 28 | HUMAN | PMSF | 67.5 |

Stabilized prolactin calibrators according to the invention were also prepared by adding 30 ng/ml human prolactin to a matrix (pH 7.5) of 0.05 M tris(hydroxymethyl)-aminomethane containing 0.1 mole/liter NaCl, and 0.3 percent in one case, 1.0 percent in a second case, and 3.0 percent in a third case of bovine serum albumin. Assays of samples of these stabilized calibrators after heat stressing for one week at 37° in comparison with assays of samples stored for one week at 2°-8° indicated that the stabilities of the samples containing 1.0 percent and 3.0 percent of bovine serum albumin were about comparable, and were also about comparable to the stability of the sample which contained 2.0 percent of bovine serum albumin (produced as described in the foregoing Example). The sample which contained 0.3 percent of bovine serum albumin was found to be less stable than the other two, but significantly increased in stability by the bovine serum albumin therein.

It will be appreciated from the foregoing data that the instant invention is a stabilized prolactin calibrator having a pH from about 5.5 to about 9.0, and consisting essentially of prolactin in a matrix of tris-(hydroxymethyl)-aminomethane and 0.3 to 4 percent of bovine serum albumin. The prolactin content of the calibrator can vary as required, depending upon the concentration of prolactin in the sample to be assayed, usually being not greater than 1 mg/ml and most often not greater than 100 mg/ml. The tris-(hydroxy-methyl)-aminomethane in the calibrator is preferably from about 0.01 M to about 0.2 M, most desirably about 0.05 M. Preferably, the pH of the calibrator is from about 6.0 to about 8.0, and the bovine serum albumin content thereof is from about 0.3 percent to about 3 percent. Most desirably, the pH is from about 7.0 to 7.5. Preferably, also, the calibrator contains from about 0.01 percent to about 0.2 percent of sodium azide, which acts as a preservative, and from about 0.01 to about 0.2 mole/liter of sodium chloride.

It will also be appreciated that the solution of the instant invention can be used to prepare calibrators for any kind of an immunoassay for prolactin. The following discussion of various kinds of immunoassays (in which the terms defined below have the meanings stated) is presented to explain the broad range of procedures where the calibrators are useful.

The term "determinants" refers to those regions of the analyte or other specific binding member which are intimately involved in specific binding reactions which are typified by the immunoreactive binding of antigens and antibodies. In essence, the determinants differentiate antigens, and therefore, antibodies from one another on the basis of immunological specificity.

The "analyte-analog" refers to a molecule which has substantially the same spatial and polar organization as one or more determinants of the analyte of interest. This duplication of the determinant(s) enables the analyte-analog to mimic the specific binding characteristics of the analyte. Therefore, the analyte-analog can bind to an analyte-specific binding member. In addition, the analyte-analog can be modified so that, while it is not identical to the analyte, it includes the necessary determinant(s) for binding to the analyte-specific binding member.

The term "specific binding member" refers to a member of a specific binding pair, i.e., two different molecules wherein one of the molecules through chemical or physical means specifically binds to the second molecule. Immunoreactive specific binding members include antigens, haptens, antibodies, and complexes thereof including those formed by recombinant DNA methods or peptide synthesis. An antibody can be a monoclonal or polyclonal antibody, a recombinant protein or a mixture or mixtures or fragment or fragments thereof, as well as a mixture of an antibody and other specific binding members. The details of the preparation of such antibodies and their suitability for use as specific binding members are well known to those skilled in the art.

The term "label" refers to any substance which is attached to a specific binding member and which is capable of producing a signal that is detectable by visual or instrumental means. Various suitable labels with which the prolactin solutions of the present invention can be used include chromogens; catalysts; fluorescent compounds; chemiluminescent compounds; radioactive labels, direct visual labels including colloidal metallic and non-metallic particles, dye particles, enzymes or substrates, or organic polymer latex particles; liposomes or other vesicles containing signal producing substances; and the like.

Many enzymes suitable for use as labels are disclosed in U.S. Pat. No. 4,275,149 columns 19-23, which is incorporated herein by reference. Also, an example of an enzyme/substrate signal producing system useful in the present invention is the enzyme alkaline phosphatase and the substrate nitro blue tetrazolium-5-bromo-4-chloro-3-indolyl phosphate or a derivative or analog thereof.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this reaction.

A visually detectable, colored particle can be used as the label component of the indicator reagent, thereby providing for a direct colored readout of the presence or concentration of the analyte in the sample without the need for further signal producing reagents. Materials for use as the colored particles are colloidal metals, such as gold, and dye particles as disclosed in U.S. Pat. Nos. 4,313,734 and No. 4,373,932. The preparation and use of non-metallic colloids, such as colloidal selenium particles, are disclosed in U.S. patent application Ser. No. 072,084, now U.S. Pat. No. 4,954,452, filed Jul. 9, 1987, commonly assigned herewith now U.S. Pat. No. 4,954,452.. The use of colloidal particle labels in immunochromatography is disclosed in U.S. patent application Ser. No. 072,459, filed Jul. 13, 1987, now U.S. Pat. No. 5,120,643, and organic polymer latex particles for use as labels are disclosed in U.S. patent application Ser. No. 248,858, filed Sep. 23, 1988, both commonly assigned herewith.

The term "indicator reagent" refers to a label attached to a specific binding member. The indicator reagent produces a detectable signal at a level relative to the amount of an analyte in the test sample. Generally, the indicator reagent is detected or measured after it is captured on a solid phase material, but unbound indicator reagent can also be measured to determine the result of an assay.

The specific binding member of the indicator reagent is capable of binding either to the analyte as in a sandwich assay, to the capture reagent as in a competitive assay, or to an ancillary specific binding member as in an indirect assay. The label, as described above, enables the indicator reagent to produce a detectable signal that is related to the amount of analyte in the test sample. The specific binding member component of the indicator reagent enables the indirect binding of the label to the analyte, to an ancillary specific binding member or to the capture reagent. The selection of a particular label is not critical, but the label will be capable of generating a detectable signal either by itself, such as a visually detectable signal generated by colored organic polymer latex particles, or in conjunction with one or more additional signal producing components, such as an enzyme/substrate signal producing system. A variety of different indicator reagents can be formed by varying either the label or the specific binding member; it will be appreciated by one skilled in the art that the choice involves consideration of the analyte to be detected and the desired means of detection.

The term "capture reagent" refers to an unlabeled specific binding member which is usually, but not in every case, attached to a solid phase. The attachment of the components is essentially irreversible and can include covalent mechanisms. The capture reagent is used to facilitate the observation of the detectable signal by substantially separating the analyte and/or the indicator reagent from other assay reagents and the remaining test sample. The specific binding member of the capture reagent can be specific either for the analyte as in a sandwich assay, for the indicator reagent or analyte as in a competitive assay, or for an ancillary specific binding member which itself is specific for the analyte, as in an indirect assay.

The term "ancillary specific binding member" refers to any member of a specific binding pair which is used in the assay in addition to the specific binding members of the capture reagent and the indicator reagent. For example, in an indirect assay an ancillary specific binding member may bind the analyte as well as a second specific binding member to which the analyte itself cannot attach, or in an inhibition assay the ancillary specific binding member may be a reference binding member, as described below. One or more ancillary specific binding members can be used in an assay.

The term "solid phase" refers to any material which is insoluble, or can be made insoluble by a subsequent reaction. An assay device with which prolactin solutions of the present invention can be used can have many configurations, several of which are dependent upon the material chosen as the solid phase. For example, the solid phase can include any suitable porous material. By "porous" is meant that the material is one through which liquids can flow and can easily pass. The solid phase can include a fiberglass, cellulose, or nylon pad for use in a pour and flow-through assay device having one or more layers containing one or more of the assay reagents; a dipstick for a dip and read assay; a test strip for wicking (e.g., paper) or thin layer chromatographic (e.g., nitrocellulose) techniques; or other porous material well known to those skilled in the art. The solid phase, however, is not limited to porous materials. The solid phase can also comprise polymeric or glass beads, microparticles, tubes, sheets, plates, slides, wells, tapes, test tubes, or the like, or any other material which has an intrinsic charge or which can retain a charged substance.

It will be appreciated that various changes and modifications can be made from the details of the invention as described in the foregoing example and as discussed above without departing from the spirit and scope thereof as defined in the following claims.

We claim:

1. A stabilized prolactin solution having a pH from about 5.5 to about 9.0, and consisting essentially of prolactin in a matrix of tris-(hydroxymethyl) aminomethane and about 0.3 to 4 percent of bovine serum albumin.

2. A stabilized prolactin solution as claimed in claim 1 wherein the tris (hydroxymethyl) aminomethane is from about 0.01 M to about 0.2 M.

3. A stabilized prolactin solution as claimed in claim 2 wherein the bovine serum albumin content is from 1 to about 3 percent.

4. A stabilized prolactin solution as claimed in claim 3 which has a pH from about 6.0 to about 8.0.

5. A stabilized prolactin solution as claimed in claim 3 which has a pH from about 7.0 to about 7.5.

6. A stabilized prolactin solution as claimed in claim 4 which additionally contains from about 0.01 percent to about 0.2 percent of sodium azide.

7. A stabilized prolactin solution as claimed in claim 4 which additionally contains from about 0.01 to about 0.2 mole/liter NaCl.

8. A stabilized prolactin solution as claimed in claim 6 which additionally contains from about 0.01 to about 0.2 mole/liter NaCl.

* * * * *